United States Patent [19]

Allison

[11] Patent Number: 5,160,413
[45] Date of Patent: Nov. 3, 1992

[54] MICRO-DISTILLATION PROCESS FOR CYANIDE

[75] Inventor: Joe D. Allison, Ponca City, Okla.
[73] Assignee: Conoco Inc., Ponca City, Okla.
[21] Appl. No.: 568,925
[22] Filed: Aug. 16, 1990
[51] Int. Cl.⁵ .......................... B01D 3/00; C01C 3/02
[52] U.S. Cl. ........................................ 203/35; 203/36; 203/37; 203/39; 203/40; 203/86; 203/95; 203/DIG. 2; 203/DIG. 22; 159/DIG. 27; 202/197; 202/200; 202/267.1; 422/101; 422/103; 423/364
[58] Field of Search ............ 203/40, 86, 39, 99, 203/DIG. 2, 29, DIG. 22, 37, 35, 34, 36; 202/197, 182, 237, 200, 266, 267.1; 423/364; 422/101, 103; 159/DIG. 27, DIG. 28; 210/640, 500.27, 500.36

[56] References Cited

U.S. PATENT DOCUMENTS

| | | | |
|---|---|---|---|
| 3,544,281 | 12/1970 | Phillips | 422/103 |
| 4,265,857 | 5/1981 | Kelada | 422/101 |
| 4,390,500 | 6/1983 | Miskinis | 422/103 |
| 4,783,318 | 11/1988 | Lapakko | 422/103 |
| 4,789,526 | 12/1988 | Matkovich | 422/101 |
| 4,803,053 | 2/1989 | Williamson | 422/103 |
| 4,863,610 | 9/1989 | Campbell | 422/101 |
| 4,990,253 | 2/1991 | Vcelka | 422/101 |
| 5,022,967 | 6/1991 | Stieg | 422/101 |

OTHER PUBLICATIONS

*What's New For The Laboratory*, Scientific Glass Apparatus Co., Inc., Bloomfield, N.J., No. 25, 1955, p. 5.
Lachat Instruments.
Chemical Abstract vol. 93:53572g (1980).
Chemical Abstract vol. 106:167950d (1987).
Chemical Abstract vol. 90:173920m (1979).
Chemical Abstract vol. 73:62394x (1970).
Chemical Abstract vol. 74:130208n (1971).
Chemical Abstract vol. 90: 109668h (1979).

Primary Examiner—Wilbur Bascomb, Jr.

[57] ABSTRACT

Micro-distillation apparatus is provided for analyzing acidic anions in which the acidic anion sample is placed in a lower elongated member in water containing an acidifying material, upon heating the acidic anion leaves the lower member as a gas, passing through a permeable membrane into an upper elongated member containing a material which converts the acidic anion to a salt and the salt is recovered for analysis. The micro-distillation apparatus is sized so that a number of samples can be heated in a small heating member, such as a hot block heater.

12 Claims, 1 Drawing Sheet

MICRO-DISTILLATION PROCESS FOR CYANIDE

BACKGROUND OF THE INVENTION

Cyanide distillations are currently carried out using the classical distillation arrangement. This consists of a large flask (typically one liter), a condenser and for cyanide a receiver flask. Also required, is a vacuum source since air is swept through the flask during the distillation. The sample to be distilled which is typically is a mixture of the cyanide, water and an acidifying agent is usually present in an amount of about 500 ml.

It would be desirable to provide a distillation system which could be carried out in micro apparatus using very small samples so that a large number of these cyanide samples as well as samples of other acidic anions could be processed at the same time.

Prior Art

A publication by Lachat Instruments (undated) which discloses a Micro-Dist ™ System described as suitable for the rapid distillation of cyanide and phenolics. The system is described as a disposable distillation tube assembly (patent pending) wherein a sample is dispensed into a sample tube which is then inserted into a collector tube containing a hydrophobic membrane. The tubes are then inserted into a heating block which accommodates 21 samples where the sample in each tube is boiled with the resulting vapor passing through the membrane into the collecting tube.

Chemical Abstract vol. 93: 53572q (1980) Determination of cyanides by continuous distillation and flow analysis with cylindrical amperometric electrodes. Pihlar, B.; Kosta, L. (Dep. Chem., Edvard Kardelj Univ., Ljubljana, Yogoslavia). Anal. Chim. Acta 1980, 114, 275-81 (Eng). A continuous system for the detn. of free and complex CN was developed. HCN is released in an acidic soln. in a countercurrent system operated by a peristaltic pump, absorbed in dil. NaOH, and then fed into the amperometric detector with a cylindrical Ag flow through electrode. The parameters affecting the release and absorption of CN, as well as the electrode response and sensitivity, are described. Differentiation between total CN and strongly bound metal CN complexes is achieved by UV decompn. of the complexes.

Chemical Abstract vol. 106: 167950d (1987)—Simple determination of minute amounts of chloride ion in plating solutions using a simple distillation apparatus for total-cyanide analysis. Nagashima, Shigeru; Ozawa, Toshio (Tokyo Metrop. Ind. Tech. Inst., Tokyo, Japan). Jitsumu Hyomen Gijutsu 1985, 32(10), 562-5 (Japan). Cl was oxidized by $H_2SO_4$ and $KMnO_4$ to $Cl_2$ which was distd. and absorbed in a soln. contg 2,2'-azinobis(3-ethyl-6-benzothiazoline-sulfonic acid). The absorbance at 415 nm ($\lambda$max) of the soln. was measured. Cl 0-80 ml/L could be detd. in 1 mL plating soln. with an error of 5-10%.

Chemical Abstract vol. 90: 173920m (1979)—Apparatus for the removal of hydrogen cyanide from waste gases from acrylonitrile fractional distillation. Bachowski, Andrzej; Tarnowski, Andrzej; Pawlus, Jozef; Musial, Bronislaw; Kowalski, Mieczyslaw; Wachowicz, Stanislaw; Horodyski, Stanislaw; Kras, Jan (Zaklady Azotowe im. Feliksa Dzierzynskiego) Pol. 85,076 (Cl. C07C121/32), Feb. 26, 1977, Appl. 156,324, Jun. 28, 1972; 3 pp. Waste gases from the distn. of acrylonitrile ∂107-13-1], which is prepd. by treating HCN with $C_2H_2$ are treated with water contg. a HCN polymn. inhibitor ($H_3PO_4$ or AcOH [64-19-7]) to absorb HCN in an absorber with a reflux condenser. The aq. 20% soln. of HCN obtained in the absorption is recycled to the acrylonitrile manufg. process. The HCN free gases are released into the air or burned.

Chemical Abstract vol. 73: 62394x (1970)—Recovery of cyanide ions by distillation. Gregorowicz, Zbigniew; Kulicka, Joanna; Czerniec, Jerzy; Gorka, Piotr (Politech. Slaska, Gliwice, Poland). Zesz. Nauk. Politech. Slask., Inz. Sanit. 1970, No. 16, 139-48 (Pol). The factors affecting the recovery of CN from aq. solns. by distn. in the presence of added $MgCl_2$, $HgCl_2$, and an acid were investigated in connection with the anal. of effluents contg. cyanide compds. The liberated HCN was collected in NaOH soln. Air or N proved suitable for use in the distn., but $CO_2$ passed through the test soln. caused difficulties in the subsequent detn. of CN. Good CN recoveries were obtained by subjecting 250 ml portions of solns. contg. free or complexed CN to distn. for 15 min at a temp. held const. at ~100°, in the presence of 50 ml of 1:1 $H_3PO_4$ or $H_2SO_4$, 20 ml of $HgCl_2$ soln. (34 g $HgCl_2$ in 500 ml $H_2O$), and 10 ml of $MgCl_2$ soln. (31 g $MgCl_2 6H_2O$ in 100 ml $H_2O$), with N bubbled through at the rate of 50-100 ml/min. The HCN was collected in 50 ml of 0.1 N NaOH. Free CN present in the solns. could be sep. recovered by conducting the distn. with tartaric acid in place of the $H_3PO_4$ or $H_2SO_4$.

Chemical Abstract vol. 74: 130208n (1971) Determination of small amounts of cyanide in the presence of ferrocyanide by distillation under reduced pressure. Roberts, R.F.; Jackson, Barry (Res. Dev. Dep., Imp.-Chem. Ind. Ltd., Northwich/Cheshire, Engl.). Analyst (London) 1971, 96(1140), 209-12(Eng). In the detn. of $\geq 0.033$ mg CN/l. in effluents and water, the decompn. of $[Fe(CN)_6]^4$ can be completely prevented by distg. CN in vacuo in the presence of $Zn(OAc)_2$. CN in the distillate was detd. by the pyridine pyrazolone spectrophotometric method. However, $[Fe(CN)_5CO]^3$ and $[Fe(CN)_5NO]^2$ were partly decompd. during the distn.

Chemical Abstract vol. 90: 109668h (1979)—Cyanide distillation apparatus. Anon. (India). Chem. Petro.-Chem. J. 1978, 9(2), 51-2 (Eng). For detg. CN in wastewaters, air is drawn through the acidified sample in a heated round bottomed flask, then through a condenser, and into a NaOH soln. for absorption. The latter soln. is used for detg. the CN by a conventional method. The recovery of CN with this app. was approx. the same as that with a com. available app.

THE INVENTION

The invention comprises a micro-distillation article of manufacture which includes a lower acid-resistant elongated member sealed at one end and open at the other end which is connected by an acid-resistant coupler to a second upper acid-resistant elongated member which is threaded at the connected end and open at the other end. An acid-resistant membrane which is permeable to acid gases is positioned between the coupled ends of the two members. An acid anion sample to be distilled is placed in the lower member with water and an acidifying agent. The assembled article of manufacture is placed in a heating member to vaporize the acid which is formed in the sample, with the vapors passing into the upper member through the acid-resistant membrane into a liquid salt-forming material where the acid is converted to a salt; wherein the cross-section of each member is between about 15 and about 2000 $mm^2$ and the length of the article of manufacture is between about 150 and about 400 mm.

BRIEF DESCRIPTION OF THE DRAWING

The drawing is an exploded schematic diagram of a micro-distillation apparatus which illustrates the articles of manufacture of the invention.

DETAILED DESCRIPTION OF THE INVENTION

Figure 1:
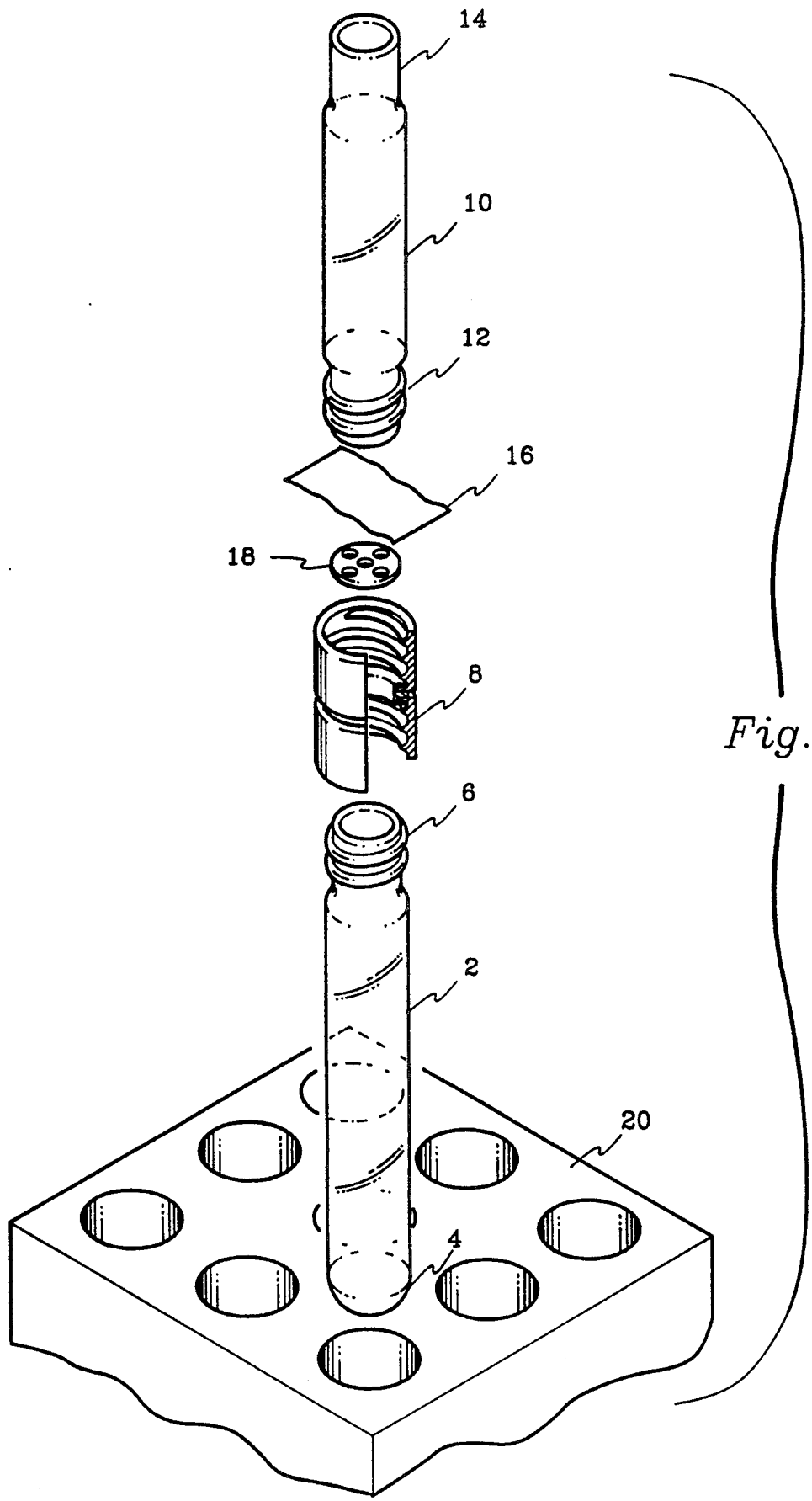

The invention is best described by reference to the drawing. Referring now to FIG. 1, there is shown a lower elongated acid-resistant member 2 which is closed at one end 4 and threaded at the other end 6. This member is joined by an acid-resistance coupler 8 to an upper elongated acid-resistant member 10. This member is threaded at the coupled end 12 and opened at the other end 14. A permeable membrane 16 is placed over the threaded end 12 of upper member 10 before coupling. Also, preferably a perforated acid-resistant disk 18 is placed between membrane 16 and the upper portion of coupler 8 before the two members are coupled.

The elongated acid-resistant members which make up the micro-distillation apparatus may be made up of any materials which are resistant to the components contained in the sample to be distilled and which are of suitable composition to resist the temperatures employed in the distillation. Glass is preferred because the reactants contained in the distillation apparatus and the mechanism of the distillation is readily visible through the glass. However, members constructed of other materials such as plastics or resins or even metal may be used within the scope of the invention. While the elongated members are preferably circular in shape they may have an elliptical or even a square configuration or any other cross section which is suitable to hold and receive the sample to be distilled. While the upper and lower members of the micro-distillation apparatus are usually of the same cross section, this is not required and either member may be larger in cross section than the other member. It is not necessary that the upper and lower members be of uniform cross-section over their entire lengths. For example, the lower portion of the lower member can be of larger cross-section than the upper portion; however, such a configuration would reduce the number of micro-distillation units which could be placed in a heating member and thus would not be desireable.

One object of the invention is to size the lower and upper members of the micro-distillation apparatus as small as possible and still obtain effective distillation. This enables a large number of the distillation units to be placed in a single heating member 20 for carrying out the distillations simultaneously. Usually the cross section of the members will be not less than about 15 mm$^2$, more usually between about 200 and about 2000 mm$^2$ and preferably between about 200 and about 300 mm$^2$. The length or height of the micro-distillation apparatus is also preferably minimized, however, this is not as important a factor as the cross section of the members. Usually, the assembled micro-distillation unit will have a height of between about 150 and about 400 mm, preferably between about 200 and about 250 mm. The upper and lower members of the micro-distillation unit may be equal in length, however, usually the lower member is longer for reasons which will be subsequently described.

A variety of acidic anions may be distilled in the micro-distillation apparatus, including, for example, arsenate, which distills as arsine ($AsH_3$) and sulfide, which distills as hydrogen sulfide ($H_2S$) In general, any acidic anion which is volatile at the temperatures employed in the distillation process may be distilled and recovered for analysis. For the purposes of the following description of the various aspects of the invention, the discussion will be directed to the distillation of cyanide samples, however, the same apparatus and procedures will apply equally to other acidic anions.

In carrying out a distillation in the micro-distillation apparatus, a sample of the cyanide along with water and an acidifying agent is mixed together and placed in the lower elongated member. The assembled distillation apparatus is then placed in a heating member where sufficient temperature is provided to vaporize hydrogen cyanide gas from the sample mixture. The hydrogen cyanide gas passes upwardly from the lower elongated member through the permeable membrane into the upper elongated member. The upper elongated member contains a salt forming material whereby a cyanide salt is formed. After the distillation is complete, the cyanide salt is removed for analysis. The amount of cyanide obtained in the distillation based on the size of the original cyanide sample, provides the concentration of cyanide in the sample.

The cyanide sample which is to be subjected to micro-distillation may be derived from a water sample or from a solid sample. Cyanides may be found in a variety of locations, for example, in the soil, in mining waste, in refinery waste, etc. Cyanides may be formed where carbon and nitrogen come together and react or when nitrates or nitrites react with certain organic compounds. Three types of cyanides are generally subjected to micro-distillation; "free cyanides" which are such materials as sodium cyanide, hydrogen cyanide, weak complex metal cyanides with metals such as zinc or cadmium, all of the above being dissolved in water. Another group of cyanides are the "weak acid-dissociable cyanides". These include the free cyanides plus cyanides associated with metals at weak acid pH (4.5) which dissociate to give metal and cyanides ions. Usually the metals are copper, nickel or silver. A third group of cyanides are the "total" cyanides. These include both the free cyanides and the weak acid dissociable cyanides and all other cyanides associated with metals (refractory cyanides) such as iron, cobalt and gold. All of the above cyanides may be effectively distilled in the micro-distillation apparatus of the invention.

As stated previously, in carrying out the micro-distillation, the cyanide sample is combined with water and an acidifying agent and mixed thoroughly. The materials may be added together in any sequence as long as effective mixing is carried out. When the combination is subjected to heat to effect distillation, hydrogen cyanide is formed and released from the liquid as a gas. The amount of cyanide which is present in the sample mixture may vary but usually will be between about 0.025 and about 10,000 micrograms. The amount of water in the sample is usually between about 0.01 and about 50 ml and the acidifying agent is usually present in an amount between about 0.1 and about 10 ml. Thus, the total sample will vary in size from about 0.1 to 60 ml. Ordinarily, larger samples will be used with micro-distillation apparatus of larger cross section.

Strong acidifying agents are required to release the cyanide from the sample and form the hydrogen cyanide gas. Such materials as concentrated phosphoric acid (85%) and concentrated sulfuric acid (95%) are ordinarily used. When the cyanide is present as refractory cyanide, the pH of the sample must be below 2.0 in order to effect conversion of the cyanide to hydrogen cyanide gas. The acids mentioned are both iron sequestering agents which is important if iron cyanide is present in the sample since this property of the acids prevents the iron cyanide complex from reforming and tying up the cyanide.

The acids mentioned; phosphoric and sulfuric, are also used in the distillation of other acid anions such as hydrogen sulfide. When the micro-distillation process is used for the recovery of arsine concentrated hydrochloric acid or concentrated nitric acid are employed as the acidifying agents.

In order to aid in the distillation, a small amount of acid. resistant solids may be added along with the sample. Usually, only 5-10 small chips or pieces of this material are used. Glass, Teflon ®, carborundum or other acid-resistant materials are appropriate for this purpose. The presence of the solids in the sample aids in the formation and escape of the gas bubbles of HCN.

In carrying out the distillation, the temperature of the contents of the lower member is heated to above the boiling point of water, however, usually the temperature provided by the heating member is not greater than about 150° C. Boiling of the liquid sample facilitates the formation and removal of the hydrogen cyanide gas. Since the distillation is basically carried out at atmospheric pressure, some steam may also be formed in the distillation. Passage of steam through the acid-resistant membrane is not desirable. To avoid this, the lower member is made sufficiently long so that the temperature of the ambient air in contact with the upper portion of the lower member is sufficient to condense the steam which then flows back to the bottom of the lower member. If sufficient cooling can not be obtained with ambient temperature, air conditioning may be used to lower the temperature of the air or a fan may be placed near the distillation unit to increase the cooling effect of the air in contact with the lower member.

The time required to complete micro-distillation and recovery of an acidic anion from a sample will depend on the type of sample, size of sample, the particular acidic anion to be recovered and the distillation temperature employed. Usually, the micro-distillation will be completed in between about 15 and about 150 minutes.

The coupling used to connect the upper and lower members of the micro-distillation unit is acid-resistant and is preferably made from a material such as Teflon ®. In addition to Teflon ®, other types of plastics or resins or metals such as stainless steel in conjunction with a Teflon ® or other acid-resistant gasket may be used in the construction of the coupling.

The membranes used in the micro-distillation apparatus are selected from materials which are acid-resistant and are permeable to acid gases. Particularly suitable are membranes of Teflon ® tape which is available in rolls of various widths and thicknesses. Tape of a thickness between about 0.5 and about 10 mils may be used. Other types of plastics and resins which are permeable to acid gases and are acid-resistant may also be employed.

A perforated support disk may be placed between the permeable membrane and the upper end of the coupling to provide support for the membrane. This disk will normally be constructed of the same material as the coupling. The disk contains perforations to allow passage of the hydrogen cyanide gas. Usually the perforations will constitute between about 10 and about 90 percent of the disk area.

The salt forming material which is placed in the bottom of the upper acid resistant member is usually a common base such as sodium hydroxide or potassium hydroxide having a molarity of from about 0.01 to about 1.0. However, other basic materials such as calcium hydroxide or ammonium hydroxide may be also used for this purpose. The amount of salt forming material employed in the distillation is usually between about 0.5 and about 5.0 ml.

It is desirable to carry out a large number of distillations simultaneously in order to reduce the manpower required for these operations. The heating member, which in one aspect comprises a part of the inventive apparatus is adapted to hold a number of distillation units up to two dozen or three dozen or more, positioned substantially vertically in the heating member. A hot block heater, which is a conventional type of electric heater may be used for this purpose. However, other heating members may be used, for example, an oil bath with holders for each distillation unit may also be used. The heating member is preferably of a small size so that one person can readily move the unit and also can easily attend to simultaneous distillation of a number of samples. Usually, the heating member will not have an area greater than about 1 square foot. However, larger heating members up to 2 or 3 square feet in area or more may be used when very large numbers of distillations are carried out at one time.

The following example is presented in illustration of the invention.

EXAMPLE

A number of distillation runs were carried out in an apparatus corresponding to that shown in FIG. 1. In the apparatus employed, both the upper and lower members had a diameter of approximately 15 millimeters. The length of the lower member was 115 millimeters and the upper member, 70 millimeters. The overall length of the distillation unit including the Teflon ® coupler was 200 millimeters. In each distillation, the sample comprised the amount of cyanide (in the form of potassium cyanide) shown in the table; in 5 milliliters of water and 2.5 milliliters of concentrated phosphoric acid. Present with the sample were 3 or 4 carborundum chips. The upper member of the distillation unit contained 2.5 ml of 0.25 Molar sodium hydroxide. Distillation of these samples was effected in a hot block heater at 120° C. with the distillation being carried out for a period of 90 minutes after the first indication of reflux. The results of the distillations are presented in the following table.

TABLE

Percent Recovery vs. Initial Concentration of Cyanide

| [Initial] micrograms/milliliter | [Recovered], ppm | % Recovery |
|---|---|---|
| 0.10 | 0.109 | 109 |
| 0.50 | 0.47 | 94.0 |
| 1.00 | 0.98 | 98.0 |
| 5.00 | 4.84 | 96.8 |
| 10.0 | 9.30 | 93.0 |
| 50.0 | 47.3 | 94.6 |
| 100 | 98.3 | 98.3 |

TABLE-continued

Percent Recovery vs. Initial Concentration of Cyanide

| [Initial] micrograms/milliliter | [Recovered], ppm | % Recovery |
| --- | --- | --- |
| 300 | 278 | 92.7 |
| 500 | 468 | 93.6 |

It is noted that over 90 percent of the cyanide was recovered in each distillation and up to as high as 98.3 percent recovery was effected. The run at 0.10 ppm shows a recovery above 100 percent, however, this is within the accuracy of measurement of such a small quantity.

The micro-distillation apparatus of the invention has a number of advantages over conventional distillation apparatus. For example, up to 25 distillations may be carried out in the micro-distillation apparatus in the same space requirements which are necessary for a single conventional distillation. The micro-distillation apparatus also has the advantage that only very small samples of the cyanide are required to carry out an effective distillation and correspondingly only very small amounts of acidifying agent and salt forming solution are required.

While certain embodiments and details have been shown for the purpose of illustrating the present invention, it will be apparent to those skilled in the art that various changes and modifications may be made herein without departing from the spirit or scope of the invention.

I claim:

1. A process for distilling cyanide which comprises:
   (a) adding cyanide, water, and an acidifying agent to a micro-distillation apparatus which comprises lower and upper acid-resistant elongated members, said lower acid-resistant member being sealed at one end and open at the other end having a cross sectional area from about 15 mm$^2$ to about 2000 mm$^2$ and being of a length equal to or greater than said upper acid-resistant member, wherein said lower acid-resistant member is of sufficient length as to preclude the distillation of water into aid upper acid-resistant member, said upper acid-resistant member being open at both ends and having a cross sectional area from about 15 mm$^2$ to about 2000 mm$^2$, said upper and lower acid-resistant members being connectably attached by means of an acid-resistant coupler which contains an acid-resistant support disc containing holes, said disc positioned between said acid-resistant coupler and said upper member supporting a membrane permeable to acid gas, wherein said upper member contains a slat forming solution;
   (b) heating the micro-distillation apparatus to a temperature sufficient to cause the evolution of cyanide gas, which permeates the membrane, and
   (c) collecting the cyanide gas in the salt forming solution.

2. The process according to claim 1 wherein the acidifying agent is a member selected from phosphoric acid, sulfuric acid, hydrochloric acid, or nitric acid and mixtures thereof.

3. The process according to claim 1 including adding acid-resistant boiling chips to the lower elongated member.

4. The process according to claim 1 wherein the acid-permeable membrane is impermeable to the salt forming solution in the upper member.

5. The process according to claim 1 wherein the acid-permeable membrane is Teflon ®.

6. The process according to claim 1 wherein the salt forming solution is a member selected from the group consisting of sodium hydroxide, potassium hydroxide, calcium hydroxide or ammonium hydroxide and mixtures thereof.

7. The process according to claim 1 wherein the salt forming solution is a member selected from the group consisting of sodium hydroxide or potassium hydroxide and mixtures thereof.

8. The process according to claim 1 wherein from about 0.025 to about 10,000 micrograms of cyanide are added to the micro-distillation apparatus.

9. The process according to claim 1 wherein from about 0.01 to about 50 ml of water are added to the micro-distillation apparatus.

10. The process according to claim 1 wherein from about 0.1 to about 10 ml of the acidifying agent is added to the micro-distillation apparatus.

11. The process according to claim 1 wherein from about 0.5 to about 5.0 ml of the salt forming solution is added to the micro-distillation apparatus.

12. The process according to claim 1 wherein the cyanide, water and acidifying agent are heated to a temperature of from about 100° C. to about 150° C.

* * * * *